United States Patent
Marrone et al.

(10) Patent No.: US 11,987,535 B2
(45) Date of Patent: May 21, 2024

(54) UREA GRANULES COMPRISING LIGNOSULFONATE COATING

(71) Applicant: Casale SA, Lugano (CH)

(72) Inventors: Leonardo Marrone, Mercallo (IT); Andrea Beretti, Rovellasca (IT)

(73) Assignee: Casale SA, Lugano (CH)

( * ) Notice: Subject to any disclaimer, the term of this patent is extended or adjusted under 35 U.S.C. 154(b) by 0 days.

(21) Appl. No.: 17/582,751

(22) Filed: Jan. 24, 2022

(65) Prior Publication Data

US 2022/0144715 A1 May 12, 2022

Related U.S. Application Data

(62) Division of application No. 17/259,692, filed as application No. PCT/EP2019/067357 on Jun. 28, 2019.

(30) Foreign Application Priority Data

Jul. 12, 2018 (EP) ..................................... 18183134

(51) Int. Cl.
  *C05C 9/00* (2006.01)
  *B01J 2/00* (2006.01)
  (Continued)

(52) U.S. Cl.
  CPC ............... *C05C 9/005* (2013.01); *B01J 2/003* (2013.01); *B01J 2/006* (2013.01); *B01J 2/04* (2013.01); *B01J 2/16* (2013.01); *B01J 2/30* (2013.01); *C05G 3/40* (2020.02); *C05G 5/12* (2020.02); *C05G 5/38* (2020.02); *C07C 273/14* (2013.01)

(58) Field of Classification Search
  CPC .... C05C 9/00; C05G 5/12; C05G 5/30; C05G 5/35; C05G 5/36; Y10T 428/2991
  See application file for complete search history.

(56) References Cited

U.S. PATENT DOCUMENTS

| | | |
|---|---|---|
| 4,219,589 A | 8/1980 | Niks et al. |
| 4,370,198 A | 1/1983 | Dencs et al. |

(Continued)

FOREIGN PATENT DOCUMENTS

| | | |
|---|---|---|
| CN | 101613244 A | 12/2009 |
| CN | 104844316 A | 8/2015 |

(Continued)

OTHER PUBLICATIONS

Otey et al., Starch Matrix for Controlled Release of Urea Fertilizer, J. Agric. Food Chem. 1984, 32, 1095-1098 (Year: 1984).*

(Continued)

*Primary Examiner* — Hoa (Holly) Le
(74) *Attorney, Agent, or Firm* — Akerman LLP

(57) ABSTRACT

A process of granulation of a urea melt, comprising: adding a first additive containing carboxymethyl starch to one or more first stage(s) of the granulation process, to form a carcarboxymethyl starch containing inner layer of urea granules, and adding a second additive containing calcium lignosulfonate to one or more second stage(s) of the granulation process, downstream said first stages, to form granules with a coating containing calcium lignosulfonate.

4 Claims, 2 Drawing Sheets

(51) Int. Cl.
*B01J 2/04* (2006.01)
*B01J 2/16* (2006.01)
*B01J 2/30* (2006.01)
*C05G 3/40* (2020.01)
*C05G 5/12* (2020.01)
*C05G 5/30* (2020.01)
*C07C 273/14* (2006.01)

(56) References Cited

U.S. PATENT DOCUMENTS

| | | | |
|---|---|---|---|
| 4,500,336 A | | 2/1985 | Van Hijfte et al. |
| 4,587,358 A | * | 5/1986 | Blouin ............... B01J 2/30 564/63 |
| 5,472,712 A | | 12/1995 | Oshlack et al. |
| 5,997,599 A | | 12/1999 | Wommack et al. |
| 2002/0098982 A1 | | 7/2002 | Burnham |
| 2014/0187424 A1 | | 7/2014 | Norton et al. |
| 2014/0364310 A1 | | 12/2014 | Li et al. |
| 2016/0326066 A1 | * | 11/2016 | Garcia Martinez ..... C05F 11/00 |
| 2016/0332924 A1 | | 11/2016 | Garcia Martinez et al. |
| 2018/0237356 A1 | * | 8/2018 | Cotrim ..................... C05B 17/02 |
| 2020/0199034 A1 | * | 6/2020 | Sharma .................... C05D 9/02 |
| 2021/0316261 A1 | * | 10/2021 | Marrone ................ B01J 2/006 |

FOREIGN PATENT DOCUMENTS

| | | | | |
|---|---|---|---|---|
| CN | 107935703 A | | 4/2018 | |
| EP | 1743879 B1 | | 9/2011 | |
| EP | 2678097 A1 | | 1/2014 | |
| EP | 2882702 B9 | * | 10/2019 | .............. C05D 3/00 |
| WO | 02/083320 A1 | | 10/2002 | |
| WO | 2005092486 A1 | | 10/2005 | |
| WO | 2011/146027 A2 | | 11/2011 | |
| WO | WO-2015104293 A1 | * | 7/2015 | ............. C05B 17/00 |
| WO | 2020/011562 A1 | | 1/2020 | |

OTHER PUBLICATIONS

Written Opinion of the International Searching Authority issued in connection with PCT/EP2019/067357.
International Search Report issued in connection with PCT/EP2019/067357.
Database WPI, Week 201578, Thomson Scientific, London, GB; AN 2015-613391, XP002786710.
Database WPI, Week 201835, Thomson Scientific, London, GB; AN 2018-32773J, XP002786711.
International Preliminary Report on Patentability issued in connection with PCT/EP2019/067357.
Wang et al., "Research Status on Anti-Caking Agents for Compound Fertilizer," Phosphate & Compound Fertilizer, 2008, Issue 1, pp. 60-63.

* cited by examiner

UREA GRANULES COMPRISING LIGNOSULFONATE COATING

CROSS-REFERENCE TO RELATED APPLICATIONS

This patent application is a divisional of U.S. patent application Ser. No. 17/259,692, filed Jan. 12, 2021, which is a national phase of PCT/EP2019/067357, filed Jun. 28, 2019, and claims priority to EP 18183134.8, filed Jul. 12, 2018, the entire contents of all of which are hereby incorporated by reference.

FIELD OF THE INVENTION

The present invention relates to a process for granulation of urea and to a granular urea product.

PRIOR ART

Granulation is one of the known techniques to convert a highly concentrated urea-containing liquid, e.g. a urea melt, into a solid granular urea product.

An overview of the urea granulation can be found in the literature, for example in the Ullmann's Encyclopedia of industrial chemistry. Typically, the granulation of a urea melt is performed in the finishing stage of a process for the production of urea.

The urea-containing liquid may receive one or more granulation additives prior to granulation or at intermediate stages of the granulation process.

WO 2005/092486 discloses a urea granulation process wherein at least part of the additive is supplied directly to the last granulation stage; EP 2 678 097 discloses a urea granulation process wherein different granulation stages have dedicated feed lines for one or more additives.

A known granulation additive is formaldehyde. Formaldehyde provides good crushing strength, low caking tendency and good resistance to abrasion of the urea granules. The above effects come from the ability of formaldehyde to react with urea forming a polymer which acts as hardening and binding agent. In addition, formaldehyde helps the granulation process itself by limiting dust formation.

Due to its high volatility, formaldehyde is handled on industrial scale in the form of a urea-formaldehyde (UF) solution. In a typical granulation process of the prior art, a urea melt containing 96% wt (% by weight) or more of urea and less than 4% wt water is admixed with a UF solution containing about 60% wt urea, about 25% wt urea and water by balance. The amount of UF solution is in generally 0.5 to 1.7% wt based on the amount of urea melt and therefore the content of formaldehyde in the granules is generally 0.3% to 1% by weight.

However, formaldehyde has been classified as carcinogenic and its use as a granulation additive, particularly for the production of urea for agricultural use, poses serious health concerns.

In the last decade, many efforts have been carried out to replace formaldehyde but no alternative additive has been proved to be satisfactory.

SUMMARY OF THE INVENTION

The invention aims to solve the drawbacks of the prior art. In particular, the invention aims to replace the use of formaldehyde as additive in a urea granulation process, while obtaining a urea granular product with improved crushing strength and abrasion resistance, and reduced caking tendency and dust formation.

These aims are achieved with a process of granulation of a urea-containing liquid which comprises at least 96% urea by weight (urea melt), comprising: adding a first additive containing carboxymethyl starch to one or more first stage(s) of the granulation process; performing one or more second stage(s) of the granulation process downstream said one or more first stage(s); wherein no amount of said first additive is added to said one or more second stage(s) of the granulation process.

The one or more second stage(s) of the granulation process are downstream the one or more first stage(s) according to the process. This means that the second stage(s) are performed after the first stage(s). In a longitudinal granulator, said stages are ordered according to a granulation path from an inlet end to an outlet end of the granulator.

A preferred embodiment comprises the addition of a second additive, which is an anti-caking additive, to said one or more second stage(s) of the granulation process. Said second additive includes preferably calcium lignosulfonate.

Accordingly a preferred embodiment of the invention includes:

adding a first additive, which contains carboxymethyl starch, to one or more first stage(s) of the granulation process;

adding a second additive, which contains calcium lignosulfonate, to one or more second stage(s) of the granulation process;

said one or more second stage(s) of the granulation process being downstream the one or more first stage(s);

wherein no first additive is added to the one or more second stage(s) of the granulation process;

Preferably, said one or more second stage(s) of the granulation process include the last stage of the granulation process. In the preferred embodiment, this results in granules of solid urea with a coating layer added with calcium lignosulfonate and containing no carboxymethyl starch.

The one or more second stage(s) of granulation are carried out substantially in absence of the first additive, which is no longer added to said stages of granulation. Therefore, the resulting layer(s) of urea granules will contain practically no amount of the first additive.

Preferably, no second additive is added to said one or more first stage(s) of the granulation process. Accordingly, the carboxymethyl starch will be located exclusively in an inner layer of the so obtained granular urea product, while the second additive, when provided, is located exclusively in a coating layer around said inner layer.

The first additive and the second additive can be added to said stages of the granulation process by mixing with a portion of the urea-containing liquid. For example, each of said stages of the granulation process receives a portion of the urea-containing liquid mixed with the first additive and/or the second additive. In some embodiments, for example, the additives can be introduced into a header or can be added to a tank of the urea-containing liquid.

In a preferred embodiment, in the one or more first stage(s) of granulation, carboxymethyl starch is added in an amount of 0.1% to 0.8% in weight based on the amount of urea fed to said one or more first stage(s).

In the one or more second stage(s) of granulation, calcium lignosulfonate is preferably added in an amount of 0.3% to 1% in weight based on the amount of urea fed to said one or more second stage(s).

More preferably the above features of 0.1% to 0.8% of carboxymethyl starch and 0.3% to 1% of calcium lignosulfonate are combined.

The urea-containing liquid preferably contains at least 97% wt urea. In a preferred embodiment the urea-containing liquid is 97% urea and 3% water. Said urea-containing liquid with 96% or more urea is also named urea melt.

The process of granulation of the present invention may be part of a urea synthesis process. Particularly, it may be a finishing stage of the urea production process. The urea production process may include: a synthesis of urea from ammonia and carbon dioxide in a high-pressure synthesis loop; a recovery of unconverted reactants in at least one recovery section, producing an aqueous urea solution (e.g. about 70% urea and 30% water); concentration of said urea solution into a urea melt for granulation.

The carboxymethyl starch is industrially produced in the form of a solid powder. Therefore, it may be necessary to dissolve the carboxymethyl starch in a suitable solvent to obtain the first additive in a liquid form.

The first additive is preferably obtained by dissolving carboxymethyl starch in a urea aqueous solution. Said urea aqueous solution may comprise a solution taken after a recovery section of a urea plant and/or a urea-water recycle solution from a granulation scrubber. Said urea aqueous solution preferably contains up to 45% urea and balance water. The first additive is preferably produced in a stirred reactor.

An advantage of dissolving the carboxymethyl starch in a urea aqueous solution is to avoid introduction of additional water into the urea synthesis process.

In an alternative embodiment of the invention the urea-water recycle solution from the granulation scrubber (up to 45% w/w urea) is used to dissolve and dilute the carboxymethyl starch. A stream of urea melt is also used to increase the urea concentration. The advantage of this alternative embodiment is the reduced load of free ammonia sent to the granulation scrubber.

The second additive is an optional feature of the invention. Use of the second additive is generally preferred to obtain the best anti-caking effect. However the one or more second stage(s) of granulation can also be fed, for example, with a urea melt with no second additive. In embodiments with no addition of said second additive, said urea melt contains preferably at least 99.5% wt of urea. This embodiment provides a slightly higher caking index compared to the use of calcium lignosulfonate as the second additive; however it might be preferred in some cases because it enhances the whiteness of the granules.

The invention is applicable to several granulation techniques. In a preferred embodiment, the granulation process is performed in a longitudinal granulator and said stages of the granulation process are distributed over the length of said granulator.

More preferably, the granulation process is performed in a fluid bed condition. The invention is applicable however to other techniques for granulation, for example to a falling curtain granulation process.

When fluid-bed granulation is used, a particularly preferred embodiment provides that a vortex condition is established in the fluid bed, by means of appropriate feeding of a fluidizing medium, usually air. The vortex condition of the fluid bed can be realized with a transversal vortex or a double transversal vortex arrangement, meaning that the vortex has an axis substantially parallel to a main flow direction of the fluid bed. Details of a preferred vortex condition are described in WO 02/083320.

A particularly preferred embodiment includes:
feeding said urea-containing liquid into a granulation environment by means of a plurality of urea inputs, wherein each of said stages of the granulation process has a respective urea input;
the addition of the first additive and optionally of the second additive to the stages of the granulation process is performed by mixing the urea-containing liquid of selected urea inputs with said additives.

Each of said urea inputs may include a plurality of sprayers. For example each urea input includes an array of sprayers arranged around a granulator. In a longitudinal granulator the sprayers of each array may be lying on a plane perpendicular to a main flow direction.

In some embodiments, different urea inputs may have a different concentration of the first additive or the second additive, thus providing a degree of freedom in determining the concentration of the additives in the granulation stages. This may result in more elaborated layered granule, wherein several layers have different content of the first or the second additive.

Some embodiments may include the feeding of solid urea matter (e.g. urea granules) to act as starting points or seeds for the granulation process. The seeds may have a size of 0.7 to 1.6 mm and produced by a roller crusher, a pastillator, or another technology. In the granulation process, the seeds are enlarged up to a target size, e.g. around 2 to 3 mm, through a series of subsequent layers of solidification of the sprayed liquid.

In an embodiment of the invention, the seeds are urea solid particles comprising carboxymethyl starch. For example the seeds may be produced starting from a urea melt containing carboxymethyl starch. This embodiment has the advantage of increasing the crushing strength of the granules.

The granulation of the present invention can be performed in the finishing stage of a process for the production of a urea product. An aspect of the invention is a process for making a solid urea product including the described process of granulation.

An aspect of the invention is also a granular urea product according to the claims.

According to a preferred embodiment, said granule has a diameter of 2 to 3 mm. Preferably, the urea core portion has a diameter from 0.7 to 1.6 mm, the intermediate portion has a thickness from 0.6 to 1.05 mm extending up to a diameter of 2.8 mm, and the coating portion has a thickness of 0.15 mm. The intermediate portion of a urea granule may contain 0.1-0.8%(wt) of carboxymethyl starch. The coating portion may contain 0.3-1%(wt) of calcium lignosulfonate.

Said first additive and second additive are advantageously added to different stages of the granulation process, thus producing granules with layers having a different composition. In particular, the carboxymethyl starch is added at an initial stage of the granulation process thus obtaining a maximum concentration of the additive in a core region of the granules, while the calcium lignosulfonate is added at a subsequent stage of the granulation process, preferably at the end of the process, thus obtaining granules with a coating layer specifically comprising this additive.

The carboxymethyl starch acts as hardening and binding agent, while the superficial layer of the granule is added with calcium lignosulfonate which reduces the caking tendency keeping a good abrasion resistance. The coupling of these two additives gives all the expected quality requirements to the urea granules, i.e. high crushing strength, good abrasion resistance and low caking tendency.

Thanks to its good adhesive properties, the carboxymethyl starch provides a binding effect and improves the strength of the granule. The outer coating added with calcium lignosulfonate prevents the caking tendency which is a source of dust formation during storage.

The outer coating additive, in some embodiments, can also be selected to improve the feature of slow nitrogen release of the solid granules. The outer coating results in a slower release of nitrogen compared to the granules without coating. This feature is advantageous for use of the solid urea product as a fertilizer.

Preferably, the terms slow nitrogen release denote a fertilizer which submitted to the analytical standard method EN13266 delivers less than 15% (on a weight basis) of its nitrogen during the first 24 hours of the test.

The process according to the invention allows having the adhesive additive (carboxymethyl starch) only inside the granule and an anticaking agent (e.g. calcium lignosulfonate) only on the external surface.

Said additives are environmentally friendly and not classified as hazardous substances. They are effective at a concentration similar to or lower than the concentration requested by formaldehyde. They are also economically competitive with respect to UF solutions.

Further characteristics and advantages of the invention will be better elucidated with the help of the following description of illustrative and non limiting embodiments.

DETAILED DESCRIPTION OF PREFERRED EMBODIMENTS

Figure 1:
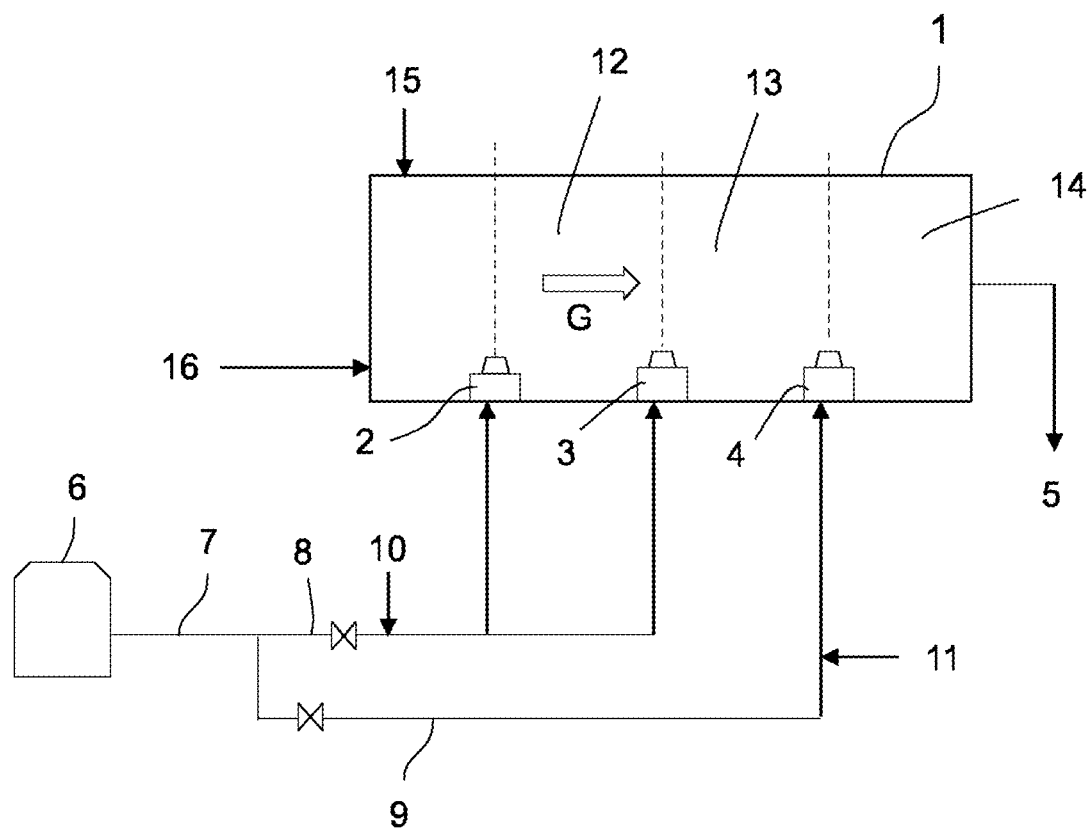
FIG. 1 is a scheme of an embodiment of the process according to the invention.

FIG. 1 illustrates a longitudinal fluid-bed granulator 1. The granulator 1 has several sets of urea melt sprayers located at different sections of the granulator itself.

FIG. 1 illustrates first sets 2, 3 of urea melt sprayers and a second set 4 of urea melt sprayers. In a real case, the number of said sets of urea melt sprayers may be for example 20 to 30. Each of the sets 2 to 4 of urea melt sprayers may include several sprayers, for example forming an array of sprayers around a vessel of the granulator 1.

The granulation process follows a main flow direction G from an inlet section to an outlet section of the granulator 1. The granulation process results in a granular product 5 which is withdrawn from the outlet section of the granulator.

A urea melt is fed from an evaporation section 6 via a main urea melt header 7. The evaporation section 6 receives a urea aqueous solution produced in a urea plant and removes water to bring the urea melt to a target concentration, e.g. 96% or more.

The main urea melt header 7 splits into a first header 8 feeding the first sets of sprayers 2, 3 and a second header 9 feeding the second set 4 of sprayers.

A first additive 10 containing carboxymethyl starch is added to the urea melt of the first header 8 and a second additive 11 containing calcium lignosulfonate is added to the urea melt in the second header 9. The flow rate of the urea melt in the headers 8 and 9 is governed by suitable flow control valves, as illustrated in FIG. 1.

Therefore, the granulation stages in the portion 12 and portion 13 of the granulator 1 are performed with urea melt containing the first additive 10, while the granulation stage in the last portion 14 (last stage of granulation) is performed with urea melt containing the second additive 11. This last stage of granulation forms a coating layer containing a desired amount of the second additive, and essentially free of the first additive.

The additives 10 and 11 may also be added directly to the sprayers or to the urea melt feeding lines of the sprayers.

FIG. 1 illustrates also an input 15 of fluidization air and an input 16 of seeds for the granulation process.

Figure 2:
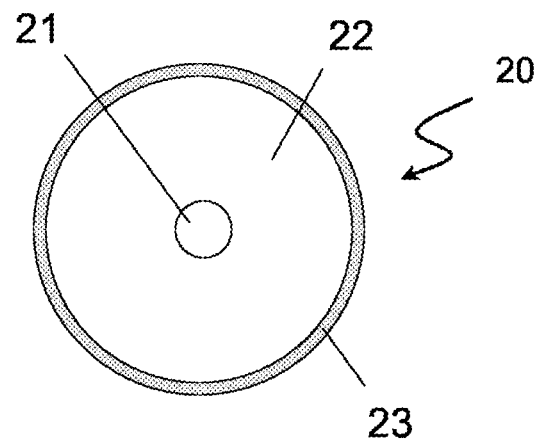
FIG. 2 is a scheme of a urea granule obtainable with the process of the invention.

FIG. 2 illustrates a granule 20 obtainable with the process. The granule includes an inner core 21, formed by a seed; a layer 22 formed in the stages 12 and 13 and containing carboxymethyl starch as a result of the addition of the first additive 10 to the urea melt 8; a coating 23 formed in the last stage 14 and containing calcium lignosulfonate as a result of the addition of the second additive 11 to the urea melt 9. The coating 23 is substantially free of carboxymethyl starch.

Figure 3:
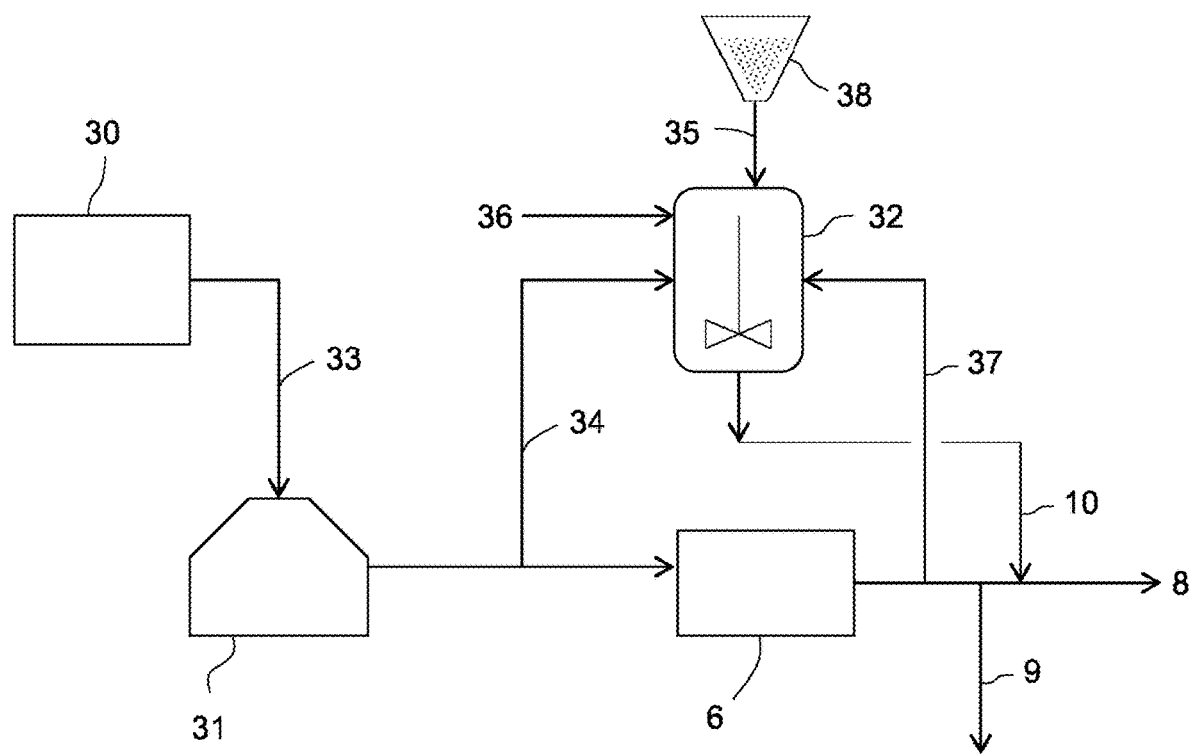
FIG. 3 is a scheme of a preferred system for metering the first additive.

FIG. 3 illustrates a preferred system for metering the first additive 10.

The figure illustrates: a low-pressure recovery section 30 of a urea production plant; a urea tank 31; a stirred reactor 32.

The low-pressure recovery section 30 produces a urea aqueous solution 33. Downstream the urea tank 31, a part of this solution is fed to the stirred reactor 32 via line 34. The stirred reactor 32 receives also the carboxymethyl starch powder 35 and optionally an amount of urea-water recycle 36 and/or an amount of urea melt via line 37.

The stream 36 contains less urea than the stream 34. The stream 37 contains more urea than said stream 34. Therefore, the streams 36, 37 can be used to adjust the concentration of urea in the reactor 32.

The carboxymethyl starch powder 35 is fed by a hopper 38 with a suitable solid feeder.

The stirred reactor produces the first additive by dissolving the carboxymethyl starch powder 35 into the aqueous urea. The temperature in the reactor 32 is preferably 60° C. to 100 ° C. and the residence time is preferably 30 min to 5 h to provide complete dissolution without deterioration of starch.

EXAMPLES

Experimental tests were carried out in batch mode.

An amount of urea seeds (about 65 kg) having a mean diameter of 1.5 mm was manually loaded in a granulation chamber and a fluidized bed was generated by blowing fluidization air. Thereafter, urea melt was fed to sprayers (about 600 kg/h) and the granulation process was started. During the granulation test the hydrostatic height of the fluidized bed was kept constant by the regulation of the overflow product valve.

Experimental tests were divided in two phases based on the additive admixed with the urea melt: in the first one the additive was a solution of carboxymethyl starch, in the second one the additive was a solution of calcium lignosulfonate. The extent of each phase was calculated on the basis of the formula:

$$d(t) = d_0 \cdot \sqrt[3]{e^{\frac{\dot{m}_{in} \cdot t}{m_0}}}$$

Wherein: d denotes the urea particles mean diameter, d(t) is the mean diameter at time t; $d_0$ is the initial mean diameter ($t=t_0$); $m_0$ the amount of urea in the granulation chamber; $m_{in}$ the urea mass flow rate; t is the time.

This relationship was used to identify the shift time of additives matching the selected diameter of the granule.

Table 2 shows the crushing strength, the caking index, the abrasion degradation and the dust formation for urea without additive and with the couple of additives (carboxymethyl starch and calcium lignosulfonate).

TABLE 2

|  | Crushing strength [kg] | Caking index [kg] | Abrasion test [%] | Dust formation [%] |
|---|---|---|---|---|
| 96% urea melt with no additive | 1.85 | 250 | 5 | 5 |
| 0.45% wt carboxymethyl starch + 99.7% urea melt with no additive | 3.3 | 50 | 2 | 1 |
| 0.45% (wt) carboxymethyl starch + 0.7% (wt) calcium lignosulfonate | 3.5 | 30 | 1.5 | negligible |

Crushing strength was tested by subjecting individual particles of urea of 3.00 mm diameter to a measured force, applied by means of an automatic metal plunger with a fixed travel speed of 10 mm/min. The force at which the particle fractures was taken as a measure of strength. The average strength of 20 particles was reported.

The caking index was measured by the following procedure: an amount of particles was kept under a pressure of about 143 kgf (2 bar applied on a surface of 70 cm²) for 24 hours at room temperature. The lump of material was then taken out and broken, the force needed for breaking the lump material was taken as measure of the caking index.

Abrasion resistance is the resistance to the formation of dust and fines as result of granule to granule and granule to equipment contact. A 100 cm3 portion of screened urea sample (between 1 mm-3.5 mm) was weighed accurately and charged to a rotary drum together with 50 steel balls of 7.9 mm diameter. The drum was closed and rotated at 60 rpm for 2.5 minutes. Thereafter the content was removed, hand screened over a 4.45 mm screen to recover the steel balls, and finally screened on a 1.00 mm screen. The material retained on the 1.00 mm screen was finally weighed accurately and degradation was calculated as follow:

Degradation, $$\% = 100 - 100 \times \frac{1 \text{ mm} < \text{Wt of fraction recovered} < 3.5 \text{ mm}}{1 \text{ mm} < \text{Wt of fraction charged} < 3.5 \text{ mm}}$$

Dust formation during the granulation process was measured as ratio between the result of the material balance around the granulation and collection chamber and the sprayed urea melt.

$$\text{Dust}[\%] = \frac{(\dot{m}_{in} \cdot \tau_{test} + m_o) - m_{discharged}}{\dot{m}_{in} \cdot \tau_{test}}$$

where $\tau_{test}$ denotes the test duration.

What is claimed is:

1. A urea granular product comprising granules made of at least 96% wt. urea with a layer containing carboxymethyl starch and a coating layer containing calcium lignosulfonate.

2. The urea product according to claim 1, wherein the carboxymethyl starch containing layer has a thickness of 0.6 to 1.05 mm and the coating layer has a thickness of 0.1 to 0.2 mm.

3. The urea product according to claim 1, wherein the carboxymethyl starch containing layer contains 0.1% to 0.8% in weight of carboxymethyl starch and the coating layer contains 0.3% to 1% in weight of calcium lignosulfonate.

4. The urea product according to claim 1, wherein the urea product is obtainable with a process of granulation of a liquid urea melt containing at least 96% wt urea, the granulation process comprising:
adding a first additive containing carboxymethyl starch to one or more first stage(s) of the granulation process;
adding a second additive, which contains calcium lignosulfonate, to one or more second stage(s) of the granulation process;
performing said one or more second stage(s) of the granulation process after said one or more first stage(s);
wherein no amount of said first additive is added to said one or more second stage(s) of the granulation process.

* * * * *